(12) United States Patent
Amin

(10) Patent No.: US 12,740,810 B2
(45) Date of Patent: Sep. 22, 2026

(54) SYSTEMS AND METHODS FOR ORTHOPEDIC TOOL CONNECTORS

(71) Applicant: Integrity Medical Services Inc., Yorba Linda, CA (US)

(72) Inventor: Nirav H. Amin, Yorba Linda, CA (US)

(73) Assignee: Integrity Medical Services Inc., Yorba Linda, CA (US)

( * ) Notice: Subject to any disclaimer, the term of this patent is extended or adjusted under 35 U.S.C. 154(b) by 0 days.

(21) Appl. No.: 19/632,934

(22) Filed: Mar. 30, 2026

(65) Prior Publication Data

US 2026/0224246 A1 Aug. 6, 2026

Related U.S. Application Data

(62) Division of application No. 19/224,327, filed on May 30, 2025, now Pat. No. 12,594,097.

(60) Provisional application No. 63/654,785, filed on May 31, 2024.

(51) Int. Cl.

| | |
|---|---|
| ***A61B 17/56*** | (2006.01) |
| ***A61B 17/16*** | (2006.01) |
| ***A61F 2/46*** | (2006.01) |
| *A61B 17/00* | (2006.01) |

(52) U.S. Cl.

CPC .......... *A61B 17/56* (2013.01); *A61B 17/1604* (2013.01); *A61B 17/1613* (2013.01); *A61B 17/1675* (2013.01); *A61F 2/461* (2013.01); *A61B 2017/00477* (2013.01); *A61F 2002/4681* (2013.01)

(58) Field of Classification Search

CPC . A61B 17/56; A61B 17/1604; A61B 17/1613; A61B 17/1675; A61B 2017/00477; A61F 2/461; A61F 2002/4681

See application file for complete search history.

(56) References Cited

U.S. PATENT DOCUMENTS

| | | | |
|---|---|---|---|
| 4,922,897 | A | 5/1990 | Sapega et al. |
| 5,112,337 | A | 5/1992 | Paulos et al. |
| 5,154,720 | A | 10/1992 | Trott et al. |

(Continued)

FOREIGN PATENT DOCUMENTS

| | | |
|---|---|---|
| CN | 104083204 | 6/2016 |
| CN | 208081271 | 11/2018 |

(Continued)

OTHER PUBLICATIONS

ANIKA Sports Medicine, ProPass™ Suture Passer, AML-900-521 Sell Sheet; 2023, downloaded on Jun. 5, 2025 from URL: https://anika.com/wp-content/uploads/2024/04/AML-900-521_ProPass-Sell-Sheet.pdf; 1 page.

(Continued)

*Primary Examiner* — Bayan Salone

(74) *Attorney, Agent, or Firm* — Knobbe, Martens, Olson & Bear, LLP

(57) ABSTRACT

A surgical tool connector that can couple with an orthopedic tool with an actuator. The connector can allow the slap hammer to quickly be coupled and decoupled with different tools. The connector can include a spring-loaded component such that the tool can be easily connected and disconnected from the slap hammer. The slap hammer can include a handle for controlling the connected tool.

11 Claims, 11 Drawing Sheets

(56) References Cited

U.S. PATENT DOCUMENTS 5,163,940 A 11/1992 Bourque
5,201,741 A 4/1993 Dulebohn
5,330,468 A 7/1994 Burkhart
5,374,269 A 12/1994 Rosenberg
5,417,684 A 5/1995 Jackson et al.
5,501,692 A 3/1996 Riza
5,709,697 A 1/1998 Ratcliff et al.
5,810,828 A * 9/1998 Lightman ............ B23B 49/008 606/80
5,817,111 A * 10/1998 Riza ................ A61B 17/06109 606/139
5,865,834 A 2/1999 McGuire
5,895,389 A 4/1999 Schenk
5,947,982 A 9/1999 Duran
5,980,538 A 11/1999 Fuchs
5,993,451 A 11/1999 Burkhart
6,022,360 A 2/2000 Reimels et al.
6,063,088 A 5/2000 Winslow
6,120,511 A 9/2000 Chan
6,254,605 B1 7/2001 Howell
6,676,668 B2 1/2004 Mercereau et al.
6,746,454 B2 6/2004 Winterbottom et al.
7,192,431 B2 3/2007 Hangody et al.
7,210,881 B2 5/2007 Greenberg
7,270,663 B2 9/2007 Nakao
7,575,578 B2 8/2009 Wetzler et al.
7,578,824 B2 8/2009 Justin et al.
7,585,305 B2 9/2009 Dreyfuss
7,771,483 B2 8/2010 Justin et al.
7,972,344 B2 7/2011 Murray et al.
7,988,693 B2 * 8/2011 Martz ............... A61B 17/1604 606/84
8,177,796 B2 5/2012 Akyuz et al.
8,282,656 B2 10/2012 Hart
8,523,872 B2 9/2013 Ek
8,690,885 B2 4/2014 Smith
8,702,731 B2 4/2014 Saliman
8,740,913 B2 6/2014 Schneider
8,888,795 B2 11/2014 Chu
9,023,056 B2 5/2015 Berberich
9,161,764 B2 10/2015 Smith
9,232,954 B2 1/2016 Steiner et al.
9,451,951 B2 9/2016 Sullivan et al.
9,668,726 B1 6/2017 Bourland, III et al.
9,687,225 B2 6/2017 Palese et al.
9,848,868 B2 12/2017 Saliman
9,877,732 B2 1/2018 Raybin et al.
10,098,646 B2 10/2018 Ardito et al.
10,278,689 B2 5/2019 Palese et al.
10,492,804 B2 12/2019 Amis et al.
10,524,778 B2 1/2020 Hendricksen et al.
10,758,251 B2 9/2020 Miller
10,765,422 B2 9/2020 Heneveld
10,799,334 B2 10/2020 Smigielski et al.
10,888,349 B2 1/2021 Pereira et al.
10,905,412 B2 2/2021 Hirotsuka et al.
10,973,511 B2 4/2021 Topper et al.
11,033,283 B2 6/2021 Mirochinik et al.
11,166,732 B2 11/2021 Maxon et al.
11,202,641 B2 12/2021 Biton et al.
11,357,517 B1 * 6/2022 Amin ................ A61B 17/1617
11,389,942 B1 * 7/2022 Stoltz .................... B25G 1/005
11,440,177 B2 * 9/2022 Sweitzer ............... A61B 17/92
11,471,150 B2 10/2022 Smith et al.
11,504,140 B2 11/2022 Fallin et al.
11,723,651 B1 * 8/2023 Simon ............... A61B 17/0482 606/144
11,903,602 B2 * 2/2024 Sullivan ........... A61B 17/32002
11,918,203 B2 * 3/2024 Murillo ............. A61B 17/0625
11,957,395 B2 * 4/2024 Zapari ................... A61B 17/92
11,986,193 B2 * 5/2024 Amin ................ A61B 17/1617
12,023,049 B2 * 7/2024 Amin ................ A61B 17/1617
12,029,412 B2 7/2024 Heneveld
12,102,338 B2 * 10/2024 Amin ................ A61B 17/1617
12,274,454 B2 * 4/2025 Amin ................ A61B 17/1617
12,285,181 B2 4/2025 Amin
12,364,487 B1 * 7/2025 Amin ................ A61B 17/1617
12,433,583 B1 10/2025 Amin
12,533,160 B2 1/2026 Amin
12,582,423 B2 3/2026 Amin
12,594,097 B2 * 4/2026 Amin .................... A61B 17/56
2002/0133165 A1 9/2002 Whittaker et al.
2003/0109888 A1 6/2003 Mercereau et al.
2004/0176771 A1 9/2004 Schmieding
2004/0249394 A1 12/2004 Morris et al.
2005/0203523 A1 9/2005 Wenstrom et al.
2005/0251146 A1 * 11/2005 Martz ............... A61B 17/1604 606/84
2005/0288690 A1 12/2005 Bourque et al.
2006/0095043 A1 5/2006 Martz et al.
2006/0173468 A1 8/2006 Simmon et al.
2006/0293689 A1 12/2006 Miller et al.
2007/0233128 A1 10/2007 Schmieding
2007/0250067 A1 10/2007 Schmieding et al.
2007/0270885 A1 11/2007 Weinert et al.
2008/0154271 A1 6/2008 Berberich et al.
2008/0183174 A1 7/2008 Sikora et al.
2008/0208221 A1 8/2008 Murray et al.
2009/0171359 A1 7/2009 Sterrett
2010/0241142 A1 9/2010 Akyuz et al.
2010/0305581 A1 12/2010 Hart
2011/0125156 A1 5/2011 Sharkey
2011/0130773 A1 6/2011 Saliman et al.
2011/0166581 A1 7/2011 Van Der Merwe et al.
2011/0238074 A1 9/2011 Ek
2011/0270280 A1 11/2011 Saliman
2012/0109136 A1 5/2012 Bourque et al.
2012/0283754 A1 11/2012 Murillo et al.
2013/0204265 A1 8/2013 Capek et al.
2014/0155899 A1 * 6/2014 Bowman ........... A61B 17/1617 606/80
2014/0276844 A1 * 9/2014 Bourque ........... A61B 17/1631 606/80
2014/0276884 A1 9/2014 Lizardi et al.
2015/0066040 A1 3/2015 Harbison et al.
2015/0133941 A1 5/2015 Saylor et al.
2015/0190147 A1 7/2015 Ferragamo et al.
2015/0345927 A1 12/2015 Bourque et al.
2015/0351777 A1 12/2015 Lizardi et al.
2016/0089161 A1 3/2016 Ardito et al.
2017/0007279 A1 1/2017 Sharma
2017/0042556 A1 2/2017 LaPrade et al.
2017/0172565 A1 6/2017 Heneveld
2017/0189036 A1 7/2017 Rajeev
2017/0245869 A1 8/2017 Mirochinik
2017/0333030 A1 11/2017 Bourland, III et al.
2018/0153572 A1 6/2018 Fojtik et al.
2020/0121474 A1 * 4/2020 Pendleton ............... A61F 2/461
2020/0275922 A1 9/2020 Valentin et al.
2020/0375615 A1 12/2020 Walker
2021/0298917 A1 * 9/2021 Sweitzer ................ B25G 1/102
2022/0110640 A1 * 4/2022 Kam ................. A61B 17/1617
2022/0117720 A1 * 4/2022 Ng ........................ A61F 2/0805
2022/0249087 A1 8/2022 Diduch et al.
2022/0296083 A1 9/2022 Wilson et al.
2022/0313336 A1 * 10/2022 Zapari .................. B25D 17/005
2023/0135885 A1 * 5/2023 Snyder ............... A61B 17/0401 606/145
2023/0157703 A1 5/2023 Torrie et al.
2023/0157808 A1 5/2023 Cole et al.
2023/0397998 A1 * 12/2023 Ekpo ...................... A61B 17/88
2024/0032911 A1 2/2024 Murillo et al.
2024/0180563 A1 * 6/2024 Amin ................ A61B 17/1617
2025/0017605 A1 1/2025 Amin
2025/0017719 A1 1/2025 Amin
2025/0366850 A1 12/2025 Amin
2025/0366869 A1 12/2025 Amin

(56) References Cited

U.S. PATENT DOCUMENTS

| | | | |
|---|---|---|---|
| 2026/0013874 | A1 | 1/2026 | Amin |
| 2026/0026801 | A1 | 1/2026 | Amin |

FOREIGN PATENT DOCUMENTS

| | | | |
|---|---|---|---|
| CN | 217853139 | U | 11/2022 |
| EP | 2419035 | | 7/2017 |
| WO | WO 2018/075615 | | 4/2018 |
| WO | WO 2025/015203 | A1 | 1/2025 |
| WO | WO 2025/251022 | A1 | 12/2025 |
| WO | WO 2025/251027 | A1 | 12/2025 |

OTHER PUBLICATIONS

Arthrex, FiberSnare® Suture. Undated; downloaded Jul. 17, 2024 from https://www.arthrex.com/knee/fibersnare; 4 pages.

DAIC—Diagnostic and Interventional Cardiology, SentreHeart Receives CE Mark for Lariat Suture Delivery Device. News Article; Oct. 28, 2015; downloaded from https://www.dicardiology.com/content/sentreheart-receives-ce-mark-lariat-suture-delivery-device; 1 page.

Espejo-Baena et al., Posterior Cruciate Ligament Reconstruction With Hamstring Tendons Using a Suspensory Device for Tibial Fixation and Interference Screw for Femoral Fixation. Arthroscopy Techniques. Feb. 1, 2017;6(1): e213-e218.

Ouyang et al., A Modfied Mason-Allen Suture Enhancement Technique (Sunglasses Loop) for Single-row Repair of Medium-to-large Rotator Cuffs. Arthros Tech. Jul. 1, 2024;13(7):103007 in 8 pages.

Petry A., SutureSnare™ Suture Passer—Product Demonstration; Anthrex Apr. 25, 2016, downloaded from https://www.arthrex.com/resources/VID1-00773-EN/suturesnare-suture-passer on Jul. 17, 2024; 4 pages.

STERIS Healthcare, Lariat® Snare. Product Details, undated, downloaded from https://www.steris.com/healthcare/products/endoscopy-devices/polypectomy-and-tissue-acquisition-devices/lariat-snare; 4 pages.

Stryker, Champion Suture Passer, 1998-2025, downloaded on Jun. 5, 2025 from URL: https://www.stryker.com/us/en/sports-medicine/products/champion-suture-passer.html; 4 pages.

Yin et al., Transtibial Pull-Out Repair of Converted Radial Tear Adjacent to Medial Meniscus Root. Arthroscopy Techniques.Jan. 1, 2020;9(1): e171-e176.

Zimmer Biomet, SpeedSnare™ Surgical Suture Passer. Website for Healthcare Professionals; undated downloaded on Jul. 17, 2024 from https://www.zimmerbiomet.com/en/products-and-solutions/specialties/sports-medicine/speedsnare-surgical-suture-passer.html, 8 pages.

Invitation to Pay Additional Fees dated Sep. 1, 2025 for Application No. PCT/US2025/031774; 12 pages.

International Search Report and Written Opinion dated Oct. 24, 2025 for Application No. PCT/US2025/031774; 22 pages.

* cited by examiner 602
604
606
112
132
600
150
160
170
130
110

1136

1135

SYSTEMS AND METHODS FOR ORTHOPEDIC TOOL CONNECTORS

INCORPORATION BY REFERENCE TO ANY PRIORITY APPLICATIONS

Any and all applications for which a foreign or domestic priority claim is identified in the Application Data Sheet as filed with the present application are hereby incorporated in their entireties by reference under 37 CFR 1.57. In particular, this application is a divisional application of U.S. patent application Ser. No. 19/224,327, filed May 30, 2025, which claims priority to the U.S. Provisional Application 63/654,785, filed May 31, 2024, which is incorporated by reference herein in its entirety.

TECHNICAL FIELD

The present disclosure relates to the field of surgical methods and devices, and more particularly to systems, methods, and devices for total knee replacement.

BACKGROUND

Certain surgical procedures, such as total knee replacement, can require a variety of tools. Slap hammers can be used to guide and control tools. The tool can be coupled with a distal end of the slap hammer and controlled using an actuator on the slap hammer. Slap hammers in the field can couple with retractors, rods, clamps, drills, pins, saws, screwdrivers, guides, trials, and/or impactors. However, users can face difficulty quickly and easily coupling and disconnecting tools with the slap hammer.

Slap hammers can apply an impacting force on a connected tool during surgery. Slap hammers typically consist of a guide rod and a sliding weight. One end of the guide rod can be connected with the surgical tool. The sliding weight may be moved to generate a force when the sliding weight contacts a stop on the end of the guide rod. The sliding weight may be repeatedly moved proximally to extract the surgical implement or distally for a precision impact.

SUMMARY

The systems, methods, and devices described herein may relate to total knee replacement devices optionally with a quick connect feature. A main body of the device can quickly couple with a variety of tools for knee extraction and replacement. For example, the main body of the device can couple with a curved osteotome, a straight osteotome, a chisel, and/or a knee extractor. The main body of the device can be a slap hammer that can guide and control each tool when connected. Among other potential uses, the total knee replacement device described herein can be used to remove an implant from a knee of a patient.

In some examples, the systems described herein can include a main body including an actuator configured to move a tool with respect to the main body; a connector, a proximal end of the connector configured to couple to a distal end of the main body, a distal end of the connector including a first engagement component; and the tool having a proximal end and a distal end, the tool including a second engagement component on the proximal end of the tool, wherein the tool is at least one of: a curved osteotome; a chisel; a straight osteotome; or a knee extractor, wherein the first engagement component of the connector is configured to couple with the second engagement component of the tool.

In some examples, the first engagement component of the connector is at least partially surrounded by a spring-loaded sheath, the spring-loaded sheath configured to retract from the first engagement component such that the first engagement component can engage the second engagement component.

In some examples, the spring-loaded sheath is configured to advance at least partially when the first engagement component is coupled with the second engagement component.

In some examples, the main body is a slap hammer.

In some examples, the first engagement component is a first hook and wherein the second engagement component is a second hook.

In some examples, the first engagement component is a hook and wherein the second engagement component is a loop.

In some examples, the first engagement component is a bayonet key and wherein the second engagement component is a bayonet lock.

In some examples, the tool is the knee extractor, and wherein actuator of the main body is configured to open and close jaws of the knee extractor.

In some examples, the first engagement component and the second engagement component are configured to couple with a collar positioned radially around the first engagement component and the second engagement component.

In some examples, the proximal end of the connector is configured to thread into the distal end of the main body.

In some examples, the devices described herein can include a shaft having a proximal end and a distal end; an engagement component on the proximal end of the shaft, wherein the engagement component of the knee extractor device is configured to couple with an engagement component of a connector; a first plate secured to the shaft; a first beam extending from the first plate; a gripper connected to the first beam; a second beam extending from the gripper; a second plate connected to the second beam, the second plate including an opening; and a synchronizer disposed at least partially in the opening of the second plate, the synchronizer including a clearance hole disposed radially around the shaft, wherein the clearance hole includes a second thread threaded to engage the first thread of the shaft, such that the second plate is prevented from moving along the shaft when the second thread engages the first thread.

In some examples, the engagement component of the knee extractor device is configured to retract a spring-loaded sheath of the engagement component of the connector such that the engagement component of the connector can engage the engagement component of the knee extractor device.

In some examples, the engagement component of the knee extractor device is configured to at least partially receive the spring-loaded sheath when first engagement component of the connector is coupled with the engagement component of the knee extractor device.

In some examples, the gripper is configured to be moved with respect to the shaft by an actuator of a handle.

In some examples, the device can include a cap on the distal end of the shaft.

In some examples, the synchronizer is movable between a first position where the second thread engages the first thread and a second position where the second thread does not engage the first thread, wherein depressing a surface of the synchronizer moves the synchronizer from the first position to the second position.

In some examples, the synchronizer is moveable to a locked position such that a surface of the synchronizer is prevented from being depressed by a portion of the second plate.

In some examples, the synchronizer is moveable to the locked position by sliding the synchronizer with respect to the second plate.

In some examples, the first plate is secured to the shaft by engaging threads.

In some examples, the device can include a second synchronizer opposite the synchronizer with respect to a central longitudinal axis Set 2

In some examples, the methods described herein can include providing a main body, a connector, and a first tool, wherein the first tool is one of a curved osteotome, a chisel, a straight osteotome, or a knee extractor, the first tool including a connection component; coupling a proximal end of the connector to a distal end of the main body; and coupling a distal end of the connector to the first tool by pushing the connection component of the first tool against a distal end of the connector to cause a spring-loaded sheath on a distal end of the connector to retract, wherein retraction of the spring-loaded sheath exposes an engagement component of the connector, the engagement component of the connector configured to couple with an engagement component of the first tool.

In some examples, the method can include disconnecting the connection component of the first tool from the connector.

In some examples, the method can include coupling the connection component of a second tool, wherein the second tool is one of a curved osteotome, a chisel, a straight osteotome, or a knee extractor.

In some examples, the method can include moving a handle on the main body to actuate the first tool.

In some examples, coupling the connector to the first tool further includes engaging a first hook on the connector with a second hook on the first tool.

In some examples, coupling the connector to the first tool further includes engaging a hook on the connector with a loop on the first tool.

In some examples, coupling the connector to the first tool further includes engaging a bayonet key on the connector with a bayonet lock on the first tool.

In some examples, disconnecting the connection component of the first tool from the connector includes disengaging a first hook on the connector from a second hook on the first tool.

In some examples, disconnecting the connection component of the first tool from the connector includes disengaging a hook on the connector from a loop on the first tool.

In some examples, disconnecting the connection component of the first tool from the connector includes disengaging a bayonet key on the connector from a bayonet lock on the first tool.

In some examples, disconnecting the connection component of the first tool from the connector includes: retracting an outer casing of the connector; tilting at least one of the connector or the connection component; and separating the connector and the connection component.

In some examples, the methods described herein can include coupling a proximal end of a connector to a distal end of a main body; and coupling a distal end the connector to a first tool, wherein the first tool is one of a curved osteotome, a chisel, a straight osteotome, or a knee extractor, the first tool including a connection component, wherein coupling the distal end of the connector to the first tool includes pushing the connection component of the first tool against a distal end of the connector to cause a spring-loaded sheath on a distal end of the connector to retract, wherein retraction of the spring-loaded sheath exposes an engagement component of the connector, coupling the engagement component of the connector with an engagement component of the first tool; disconnecting the connection component of the first tool from the connector; and coupling the connection component of a second tool, wherein the second tool is one of a curved osteotome, a chisel, a straight osteotome, or a knee extractor.

In some examples, the method can include moving a handle on the main body to actuate the first tool.

In some examples, coupling the connector to the first tool further includes engaging a first hook on the connector with a second hook on the first tool.

In some examples, coupling the connector to the first tool further includes engaging a hook on the connector with a loop on the first tool.

In some examples, coupling the connector to the first tool further includes engaging a bayonet key on the connector with a bayonet lock on the first tool.

In some examples, disconnecting the connection component of the first tool from the connector includes disengaging a first hook on the connector from a second hook on the first tool.

In some examples, disconnecting the connection component of the first tool from the connector includes disengaging a hook on the connector from a loop on the first tool.

In some examples, disconnecting the connection component of the first tool from the connector includes disengaging a bayonet key on the connector from a bayonet lock on the first tool.

In some examples, disconnecting the connection component of the first tool from the connector includes: retracting an outer casing of the connector; tilting at least one of the connector or the connection component; and separating the connector and the connection component.

DETAILED DESCRIPTION

Embodiments disclosed herein relate to devices, systems, and methods for total knee extraction. Some embodiments of devices disclosed herein relate to a device including a slap hammer, a connector, and a set of tools that can be connected to the slap hammer by the connector. Orthopedic procedures, for example total knee replacement, can require a variety of tools. Orthopedic procedures can include fixation into or onto bones of limbs, spine, pelvis, or craniomaxillofacial. This system can allow a user to quickly and efficiently couple the tools to the slap hammer. The tools can be swapped for one another using the methods described herein to reduce time taken to change tools during a procedure. The tools can include, without limitation, a knee extractor, a curved osteotome, a straight osteotome, and a chisel. The connector can allow for a force connection, for example a spring-loaded connection, so that the tools can be easily pushed into the connector.

Figure 1A:
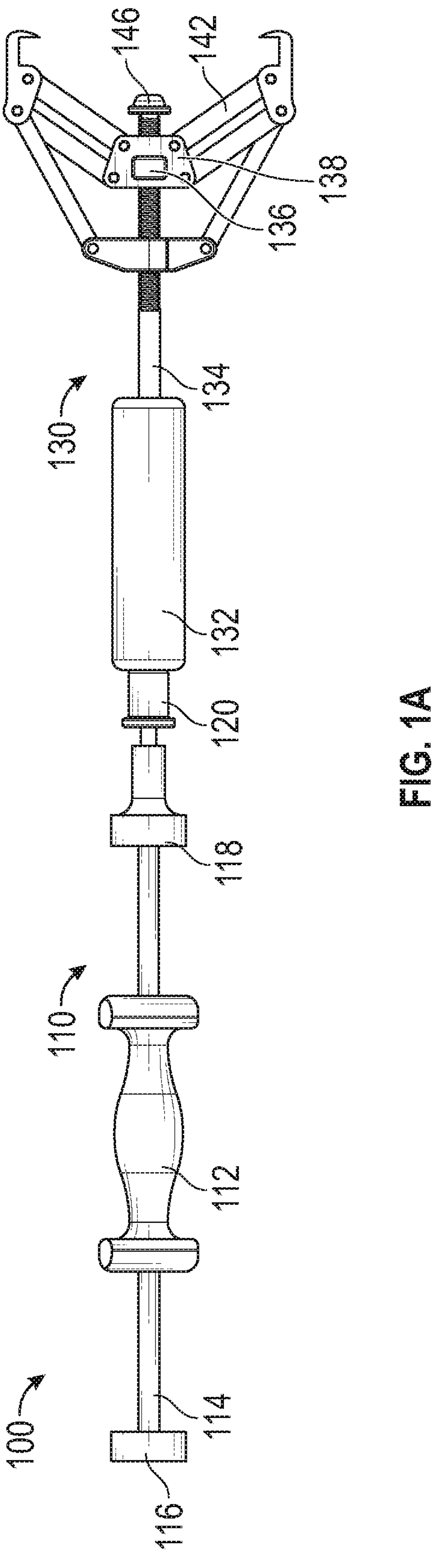
FIG. 1A shows an example of a total knee extraction system.
Figure 1B:
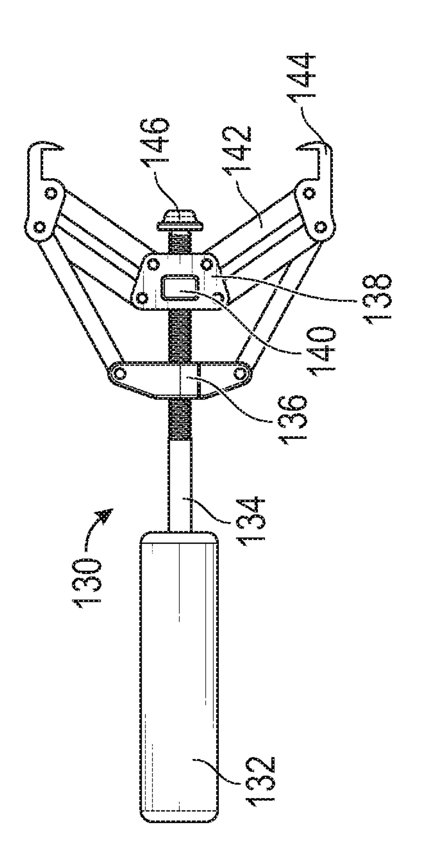
FIG. 1B shows the example of the knee extractor of FIG. 1A.
Figure 1C:
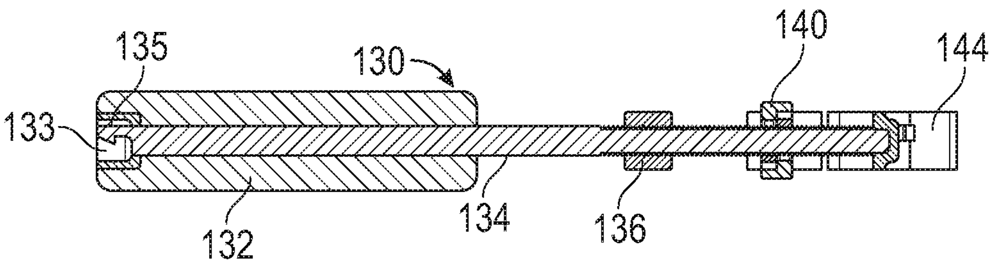
FIG. 1C shows a cross-sectional, side view of the example of the knee extractor of FIG. 1A.

FIG. 1A shows an example of a total knee extraction system 100. FIG. 1B shows the example of the knee extractor 130 of FIG. 1A. FIG. 1C shows a cross-sectional, side view of the example of the knee extractor 130 of FIG. 1A. While FIG. 1A-C illustrates a knee extractor 130, other tools, such as but not limited to a curved osteotome, a straight osteotome, and a chisel can be included.

In certain examples, the total knee extraction system 100 can include a slap hammer 110. The slap hammer 110 can include an actuator 112 configured to control a tool connected to the slap hammer 110. In some implementations, the actuator 112 can slide along a shaft 114 (e.g., axially along the shaft 114, in a proximal and/or distal direction). In some implementations, the actuator 112 can move along the shaft 114, for example in two directions, to extend and retract a tool or an element of a tool. In some examples, the actuator 112 can move along the shaft in 1-4 directions. Movement of the actuator 112 along the shaft can control the tool (e.g., close jaws, extend and/or retract the tool or an element of the tool, etc.). The actuator 112 can be a handle or trigger. In some implementations, the actuator 112 can move between a proximal stopper 116 and a distal stopper 118. The proximal stopper 116 and the distal stopper 118 can define the boundaries of movement of the actuator 112. In some implementations, a user can rotate the actuator 112 to control the tool. In some implementations, a user can rotate the actuator 112 to extend and/or retract a tool or an element of a tool.

In some examples, a connector 120 can attach to a distal end of the slap hammer 110. In some implementations, the connector 120 can temporarily attach to a distal end of the slap hammer 110. In some implementations, a proximal end of the connector 120 can partially or fully surround a circumference of the distal end of the slap hammer 110. In some implementations, the distal end of the slap hammer 110 can partially or fully surround a proximal end of the connector 120. The connector 120 can couple to the slap hammer 110 using a fastener, a clamp, a snap fit, a latch, magnetism, interlocking joints, pressure fittings, a ratcheting mechanism, or another means of connection. The connector 120 can attach to the slap hammer 110 such that it does not disconnect during use of the tool.

In some examples, the connector 120 can couple the slap hammer 110, or main body, to a tool, wherein main body can refer to the slap hammer 110, or a portion of the slap hammer 110, or to another component or mechanism, such as but not limited to a handle for a tool. In some implementations, the connector 120 can temporarily attach to a tool. As shown in FIGS. 1A and 1*i*, the tool can be a knee extractor 130. In some embodiments, the tool can be, without limitation, a curved osteotome, a straight osteotome, and a chisel. The distal end of the connector 120 can attach to a proximal end of a tool. The tool can have a connection component 132 on the proximal end. The connection component 132 of the tool can partially or fully surround the circumference of the distal end of the connector 120. In some implementations, the distal end of the connector 120 can partially or fully surround the circumference of the connection component 132 of the tool. The connector 120 can couple to the connection component 132 of the tool using a fastener, a clamp, a snap fit, a latch, magnetism, interlocking joints, pressure fittings, a ratcheting mechanism, or another means of connection. The connector 120 can attach to the connection component 132 of the tool such that it does not disconnect during use of the tool. The tool can be easily and efficiently disconnected from the connector 120. For example, a user can pull the connection component 132 of the tool from the connector 120. In some implementations, a user can engage (e.g., compress or rotate) the connection component 132 of the tool to disconnect the tool from the connector 120.

As shown in FIG. 1B, the knee extractor 130, or any other tool, can include a shaft 134 distal to the connection component 132. The shaft 134 can be at least partially or fully threaded. In some implementations, moving or engaging with (e.g., rotating, moving proximally or distally, etc.) the actuator 112 can cause the shaft 134 to rotate. The knee extractor 130, or any other tool, can include a synchronizer 136. The synchronizer 136 can include one or more plates for synchronizing or coordinating movement of elements or components of the tool (e.g., grippers). The synchronizer 136 can have a clearance hole through the center, such that the synchronizer 136 has no attachment to or engagement with the shaft 134. In some implementations, the synchronizer 136 can move along the shaft 134 as the shaft 134 rotates. In some implementations, the synchronizer 136 can lack engagement with the shaft 134. In some implementations, the synchronizer 136 can be threaded to contact and/or engage the shaft 134.

In some examples, the knee extractor 130 can include a midplate 138. In some implementations, the midplate 138 can move along the shaft 134 as the shaft 134 rotates. The midplate 138 can be threaded to engage the shaft 134 (e.g., a threaded portion of the shaft 134). The midplate 138 can include a lock 140, which can be disengaged (e.g., unlocked) or engaged (e.g., locked). As shown in FIG. 1C, the lock 140 can allow the midplate 138 to move along the shaft 134 when the lock 140 is disengaged. When engaged, the lock 140 can prevent the midplate 138 from moving along the shaft 134. For example, the lock 140 can contact the shaft 134 to cause the midplate 138 to move with the shaft 134. Unlike the midplate 138, the more proximal plate can be immovably secured or integral with the shaft 134.

In some examples, the knee extractor 130 can include one or more grippers 144. The grippers 144 can be connected to the midplate 138 and the synchronizer 136 by one or more beams 142. In some implementations, each gripper can be connected to the midplate 138 by 2 beams. In some implementations, each gripper can be connected to the midplate 138 by 1-5 beams. In some implementations, each gripper can be connected to the synchronizer 136 by 1 beam. In some implementations, each gripper can be connected to the synchronizer 136 by about 1-5 beams. The knee extractor 130 can include a shaft cap 146. The shaft cap 146 can prevent the midplate from moving past the distal end of the shaft 134.

In some examples, for example as shown with respect to FIGS. 11A-11F and 12A-12B, the midplate 138 can include one or more half nuts that can engage a thread on the shaft 134. When the half nuts are compressed, the shaft 134 can be freely moved through the midplate 138. In some implementations, lock 140 can be engaged such that the midplate 138, the half nuts can be compressed.

In certain examples, a user can rotate the actuator 112 to open and close the knee extractor 130. In an open position, the grippers 144 of the actuator 112 can be closer together. In a closed position, the grippers 144 of the actuator 112 can be farther apart. In some embodiments, a user can rotate the actuator 112 to advance the synchronizer 136 toward the midplate 138. In this example, the user can rotate the actuator 112 to retract the synchronizer 136 away from the midplate 138. In some embodiments, a user can rotate the actuator 112 to retract the midplate 138 toward the synchronizer 136. In this example, the user can rotate the actuator 112 to advance the midplate 138 away from the synchronizer 136. The jaws of the knee extractor 130 can move freely toward and away from the centerline of the extractor. Once the jaws are positioned under the knee joint, the shaft 134 can be tightened up against the knee joint. Tightening the shaft 134 can force the jaws to move towards the centerline of the knee extractor 130. The grippers 144 can squeeze the knee joint.

In examples, the tool can include a connection socket 133 on the proximal end of the connection component 132. The connection socket 133 can be integral with the shaft 134, such that the shaft 134 rotates when the connection socket 133 rotates. The distal end of the connector 120 can fit within the connection socket 133. The connection socket 133 can rotate when the connector 120 rotates. The connection socket 133 can include a hook 135, or tooth. The hook 135 can engage a hook of the connector 120. The hook 135 can form a snap fit with a hook of the connector 120. A user can backslap the tool with the connector 120 by pressing the connector 120 into the connection socket 133.

Figure 2A:
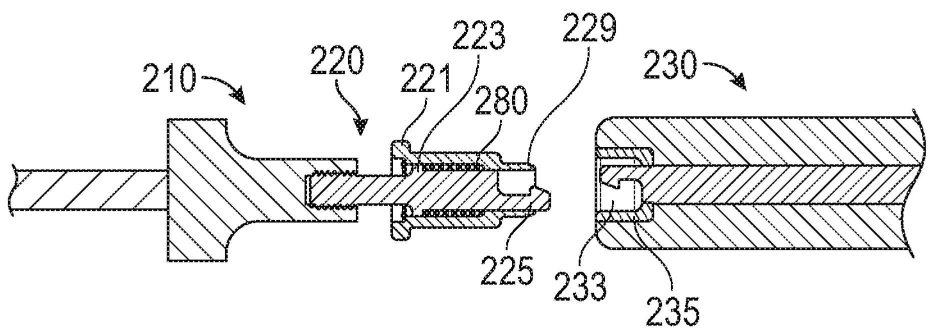
FIG. 2A shows an example of a main body and a connector disconnected from a tool connection component.
Figure 2B:
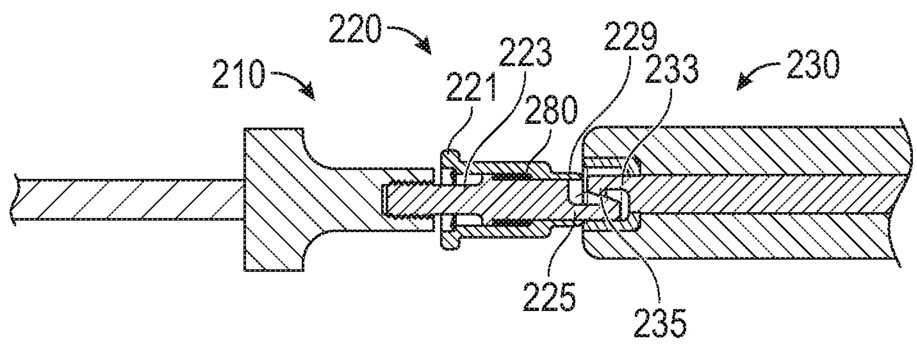
FIG. 2B shows an example of the main body and connector coupling to the tool connection component of FIG. 2A.
Figure 2C:
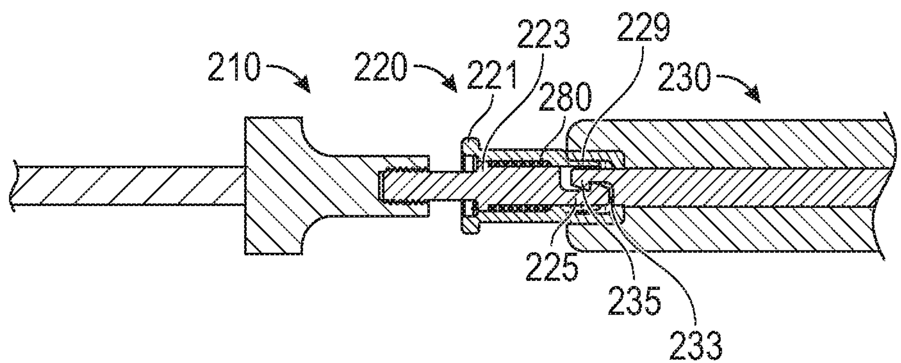
FIG. 2C shows an example of the main body and connector connected to the tool connection component of FIG. 2A.

FIG. 2A shows an example of a main body 210 and a connector 220 disconnected from a tool connection component 230. FIG. 2B shows an example of the main body 210 and connector 220 coupling to the tool connection component 230 of FIG. 2A. FIG. 2C shows an example of the main body 210 and connector 220 connected to the tool connection component 230 of FIG. 2A.

In some examples, the main body 210 can be connected to the connector 220, for example with a force-locking or form-locking connection. The proximal end of the connector 220 can lock into the distal end of the main body 210.

The distal end of the connector 220 can include a male connection component. For example, in some examples, the distal end of the connector 220 can include a hook 225, or tooth. The tool connection component 230 can include a female connection component. For example, the hook 225 of the connector can engage a hook 235, or tooth, of the tool connection component 230. The hook 235 of the tool connection component 230 can be in a connection socket 233. The connector 220 can fit within the connection socket 233 such that the hooks 225, 235 fit together. The connector 220 can fit within the connection socket 233 such that the hooks 225, 235 form a snap-fit connection. A lip 229 of the connector 220 can fit within the connection socket 233. The lip 229 can press the hook 235 of the connection component 230 against the hook 225 of the connector 220. The lip 229 can prevent the connector 220 from decoupling from the tool during use. In some embodiments, the distal end of the connector 220 can include a female connection component and the tool connection component 230 can include a male connection component. For example, the distal end of the connector 220 can include a connection socket and a hook, and the tool connection component 230 can include lips and a hook that can engage with the hook in the connection socket of the connector 230.

As shown in FIG. 2B, the hooks 225, 235 can have sloped surfaces such that they slide along each other as the connector 220 enters the connection socket 233. As shown in FIG. 2C, the hooks 225, 235 can click together when the connector 220 further enters the connection socket 233.

In some examples, the connector 220 can be spring-loaded. For example, the connector 220 can include one or more springs 280. Pushing the tool connection component 230 against the connector 220 can cause the spring 280 to compress such that the outer casing 221, or sheath, of the tool connection component 230 slides proximally toward the main body 210. Advantageously, this can expose or unsheathe the hook 225 from the sheath such that it can engage the hook 235 of the tool connection component 230. The springs 280 of the connector 220 can couple an inner component 223 to an outer casing 221 of the connector 220. The inner component 223 can be integral with the hook 225. As shown in FIG. 2A, the springs 280 of the connector can retain the inner component 223 with respect to the outer casing 221 such that the hook 225 is partially exposed from the distal end of the outer casing 221 at rest.

As shown in FIG. 2B, the connection component 230 can push the outer casing 221 of the connector 220 toward the main body 210. The springs 280 of the connector 220 can stretch as the outer casing is pushed.

As shown in FIG. 2C, once the hooks 225, 235 are coupled, the springs 280 can push the distal end of the outer casing 221 into the connection socket 233.

In some examples, as described above, the springs 280 can be configured such that pushing the connection component 230 against the connector 220 couples the tool to the connector 220. The connector 220 can be a spring-loaded connection component. To decouple the connector 220 from the connection component 230, a user can retract the outer casing 221 such that the lip 229 is outside the connection socket 233. A user can offset the connector 220 or the tool from the centerline to disengage the hooks 225, 235. A user can tilt at least one of the connector 220 or the connection component 230 and separate the connector 220 and the connection component 230.

Figure 3:
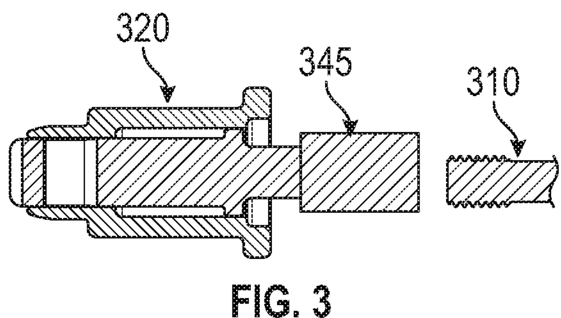
FIG. 3 shows an example of a distal end of a main body and a tool.

FIG. 3 shows an example of a distal end of a main body 310 and a connector 320.

In some implementations, the main body 310 can couple directly to the connector 320. The connector 320 can include a collar 345 which can couple with the main body 310. The collar 345 can be similar to the collar described with respect to FIGS. 7A and 7B. For example, the distal end of the main body 310 may be externally threaded and the proximal end of the collar 345 may be internally threaded. In another example, the distal end of the main body 310 may be internally threaded and the proximal end of the collar 345 may be internally threaded.

Figure 4A:
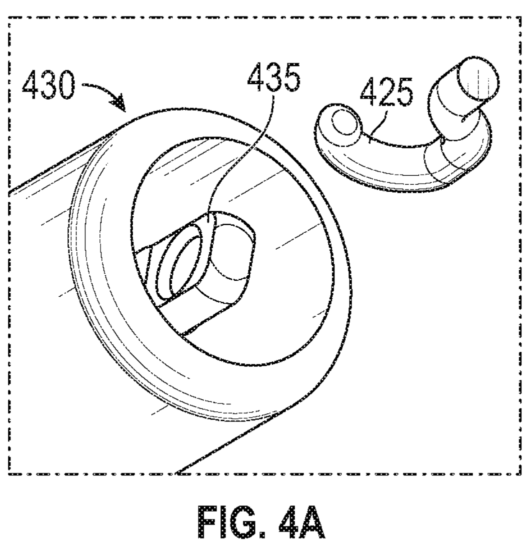
FIG. 4A shows a perspective view of an example of a hook and a connection component of a tool.
Figure 4B:
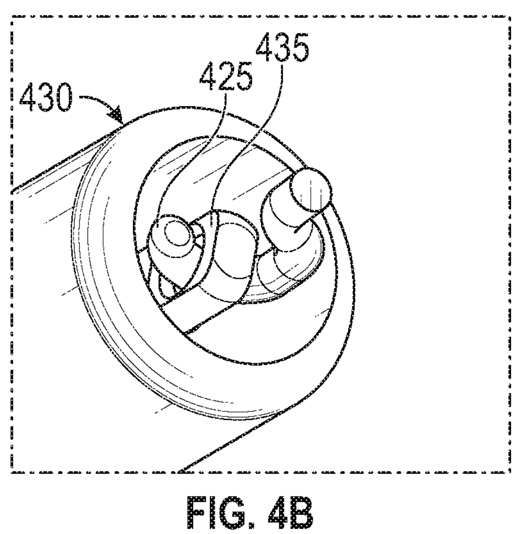
FIG. 4B shows a perspective view of the example of the hook coupled with the connection component of a tool of FIG. 4A.
Figure 4C:
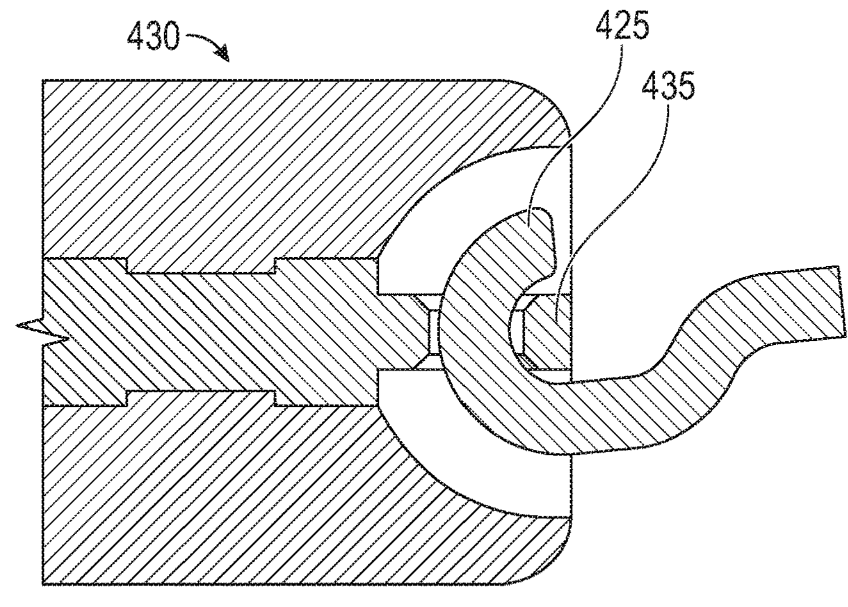
FIG. 4C shows a cross-sectional, side view of the example of the hook coupled with the connection component of a tool of FIG. 4A.

FIG. 4A shows a perspective view of an example of a hook 425 and a connection component 430 of a tool. FIG. 4B shows a perspective view of the example of the hook 425 coupled with the connection component 430 of a tool of FIG. 4A. FIG. 4C shows a cross-sectional, side view of the example of the hook 425 coupled with the connection component 430 of a tool of FIG. 4A.

In some examples, the connection component 430 of a tool can include a loop 435. The hook 425 can be attached to a connector or main body. As shown in FIGS. 4B and 4C, a user can couple the hook 425 to the loop 435 to couple the main body to the tool. Rotation of the hook 425 along the longitudinal axis of the connection component 430 can translate to rotation of the tool or an element of the tool. In some embodiments, the connection component 430 of a tool can include a hook, and the connector or main body can include a loop.

Figure 5A:
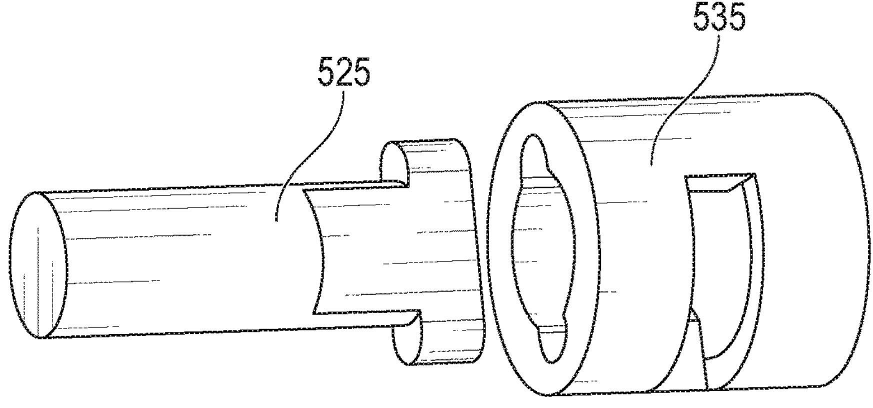
FIG. 5A shows an example of a bayonet key and a bayonet lock.
Figure 5B:
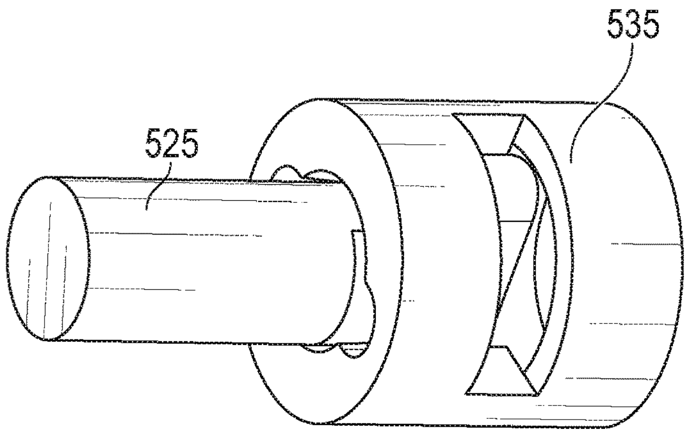
FIG. 5B shows the example of the bayonet key coupled with the bayonet lock of FIG. 5A.

FIG. 5A shows an example of a bayonet key 525 and a bayonet lock 535. FIG. 5B shows the example of the bayonet key 525 coupled with the bayonet lock 535 of FIG. 5A.

In some examples, a tool described herein can include a bayonet lock 535 or bayonet key 525 on the proximal end of the tool. A connector described herein can include a bayonet key 525 or a bayonet lock 435 on the distal end of the connector. The tool and connector can be coupled using the bayonet key 525 and bayonet lock 535. The bayonet key 525 can be inserted into the bayonet lock 535 and rotated to lock the connector to the tool. The bayonet key 525 can be prevented from rotating until the bayonet key 525 reaches the proper depth of the bayonet lock 535 to ensure the connection is at a target depth of the bayonet lock 535.

Figure 6:
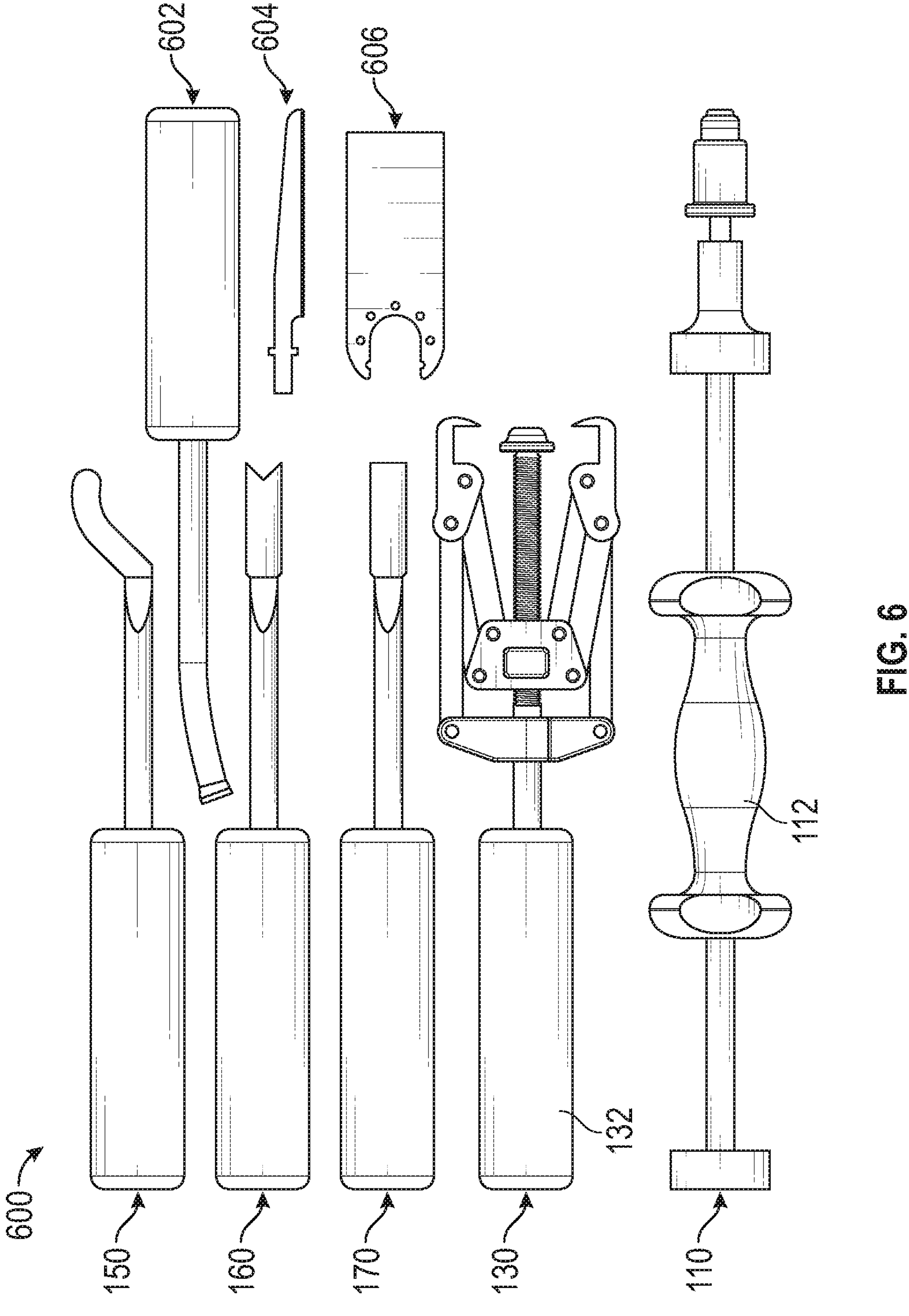
FIG. 6 shows an example knee extraction kit.

FIG. 6 shows an example knee extraction kit 600.

In some examples, the knee extraction kit 600 can include a slap hammer 110, a knee extractor 130, a curved osteotome 150, a chisel 160, and/or a straight osteotome 170. The slap hammer 110 can couple with a tool with a connection component 132. The knee extractor 130, curved osteotome 150, chisel 160, and straight osteotome 170 can each have a connection component 132. The connection component 132 can allow each tool to be connected and disconnected from the slap hammer 110. In some embodiments, tools with connection components 132 can include, without limitation, retractors, rods, clamps, drills, pins, saws, screwdrivers, guides, trials, and/or impactors.

In some examples, the slap hammer 110 can be coupled with the curved osteotome 150, chisel 160, or straight osteotome 170. The actuator 112 of the slap hammer 110 can be moved or rotated to control the tool connected to the slap hammer 110. The actuator 112 can be moved or rotated to advance, retract, or rotate the curved osteotome 150. The actuator 112 can be moved or rotated to advance, retract, or rotate the chisel 160. The actuator 112 can be moved or rotated to advance, retract, or rotate the straight osteotome 170.

In some examples, the knee extractor 130 can be used to grip or extract a knee implant. The knee extractor 130 can be used to remove a replacement knee joint that was implanted. The knee extractor 130 can be used to separate a replacement knee joint from bone that has grown into and/or onto the implant. In some embodiments, the knee extractor 130 can be used to remove implants in other parts of the body. For example, the knee extractor 130 can be used to remove implants in the elbow, shoulder, or ankle of the patient. The knee extractor 130 can partially or entirely extract at an implant from least one of the femur, the tibia, or the patella from a patient. The curved osteotome 150 can be used for precise cutting of bone during the extraction procedure. The chisel 160 can be used to efficiently break down bone during the extraction procedure. The straight osteotome 170 can be used to remove bone tissue during the extraction procedure.

In some examples, the knee extraction kit 600 can include a bone tamp 602, an oscillating saw blade 604, and/or a reciprocating saw blade 606. The bone tamp 602 can be curved. The bone tamp 602 can be used to compress bone graft material into voids left after removing damaged bone or tissue from the knee joint. The oscillating saw blade 604 and/or reciprocating saw blade 606 can be used to cut bone and surrounding tissue during the extraction procedure.

In some implementations, at least one of the knee extractor 130, curved osteotome 150, chisel 160, or straight osteotome 170 can be disposable. In some implementations, at least one of the curved osteotome 150, chisel 160, or straight osteotome 170 can be disposable. In some implementations, the connector can be disposable.

Figure 7A:
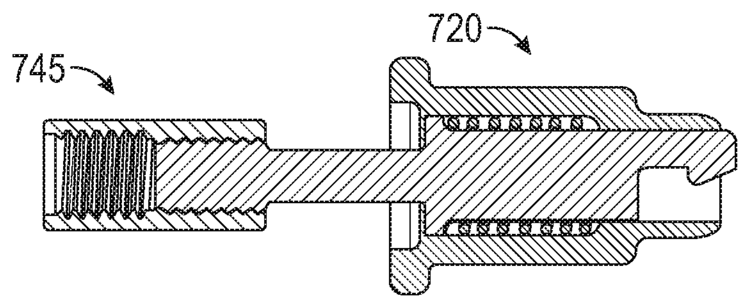
FIG. 7A shows a cross-sectional view of an example of a connector coupled to a collar for coupling to a main body.
Figure 7B:
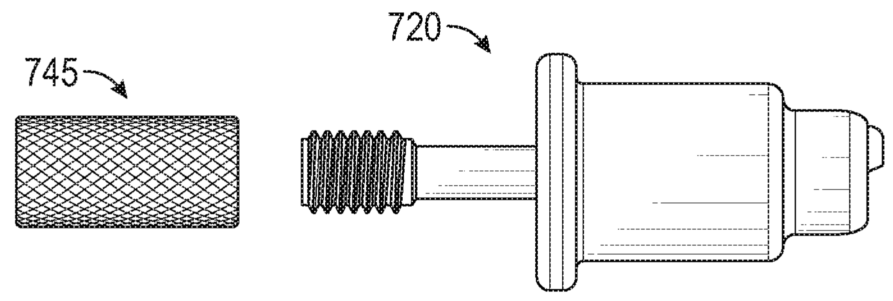
FIG. 7B shows a side view of the example of the connector and collar of FIG. 7A.

FIG. 7A shows a cross-sectional view of an example of a connector 720 coupled to a collar 745 for coupling to a main body. FIG. 7B shows a side view of the example of the connector 720 and collar 745 of FIG. 7A.

In some examples, a distal end of the collar 745 can partially or fully surround a circumference of a proximal end of connector 720. The proximal end of the collar 745 can partially or fully surround a circumference of a distal end of a main body, or slap hammer. The collar 745 can be flexible. The collar 745 can be biased to compress inward. The collar 745 can couple the main body to the connector 720. The distal end of the connector 720 can couple with a variety of tools.

Figure 8A:
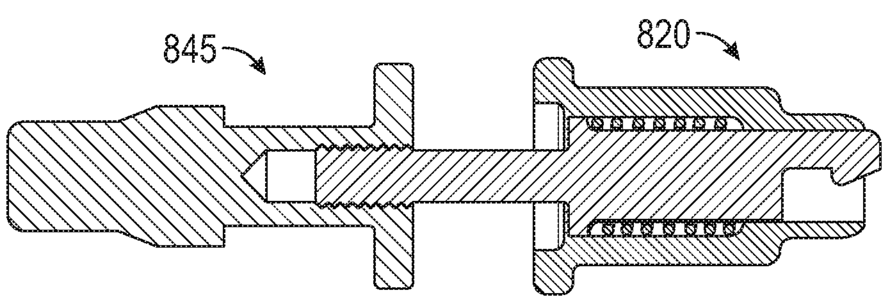
FIG. 8A shows a cross-sectional view of an example of a connector coupled to an adapter for coupling to a main body.
Figure 8B:
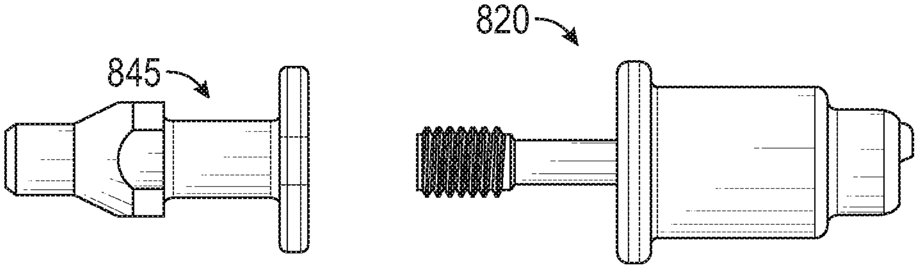
FIG. 8B shows a side view of the example of the connector and adapter of FIG. 8A.

FIG. 8A shows a cross-sectional view of an example of a connector 820 coupled to an adapter 845 for coupling to a main body. FIG. 8B shows a side view of the example of the connector 820 and adapter 845 of FIG. 8A.

In some examples, a distal end of the adapter 845 can partially or fully surround a circumference of a proximal end of connector 820. The proximal end of the adapter 845 can partially or fully surround a circumference of a distal end of a main body, or slap hammer. A distal end of the adapter 845 can be threaded to couple with the proximal end of the connector 820. The adapter 845 can couple the main body to the connector 820. The distal end of the connector 820 can couple with a variety of tools.

In some examples, the adapter 845 can be an automatic adapter. The adapter 845 can automatically connect a tool with a connection component to devices from other systems. The adapter 845 can connect a tool to a drill or another electrically powered device. The system including the adapter 845 can be used to remove an implant from a patient. In some embodiments, a slap hammer described herein can be connected to an automatic extractor using this adapter 845. The slap hammer can be used to operate the automatic extractor after being connected to the extractor using the adapter 845. Advantageously, connecting the automatic extractor to the slap hammer can provide an easier means of extraction than manual extraction.

Figure 9A:
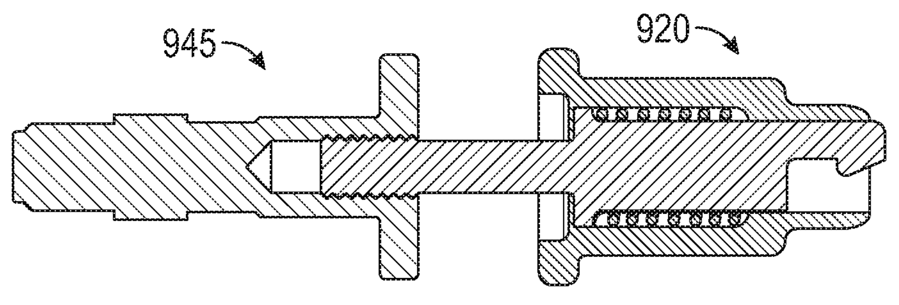
FIG. 9A shows a cross-sectional view of another example of a connector coupled to an adapter for coupling to a main body.
Figure 9B:
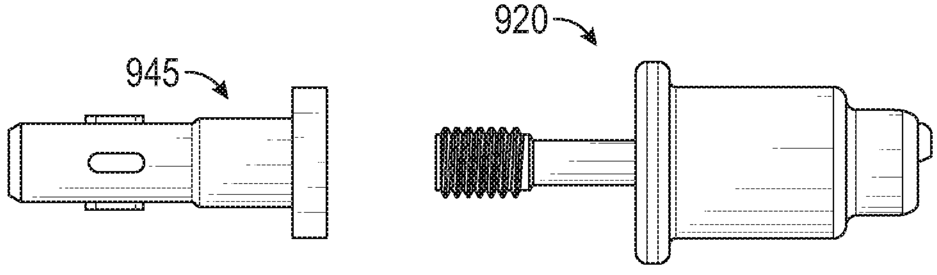
FIG. 9B shows a side view of the example of the connector and adapter of FIG. 9A.

FIG. 9A shows a cross-sectional view of an example of a connector 920 coupled to an adapter 945 for coupling to a main body. FIG. 9B shows a side view of the example of the connector 920 and adapter 945 of FIG. 9A.

In some examples, a distal end of the adapter 945 can surround a circumference of a proximal end of connector 920. The proximal end of the adapter 945 can surround a circumference of a distal end of a main body, or slap hammer. A distal end of the adapter 945 can be threaded to couple with the proximal end of the connector 920. The adapter 945 can couple the main body to the connector 920. The distal end of the connector 920 can couple with a variety of tools.

In some examples, the adapter 945 can be an automatic adapter. The adapter 945 can automatically connect a tool with a connection component to devices from other systems. The adapter 945 can connect a tool to a drill or another electrically powered device. The system including the adapter 945 can be used to remove an implant from a patient. In some embodiments, a slap hammer described herein can be connected to an automatic extractor using this adapter 945. The slap hammer can be used to operate the automatic extractor after being connected to the extractor using the adapter 945. Advantageously, connecting the automatic extractor to the slap hammer can provide an easier means of extraction than manual extraction.

Figure 10A:
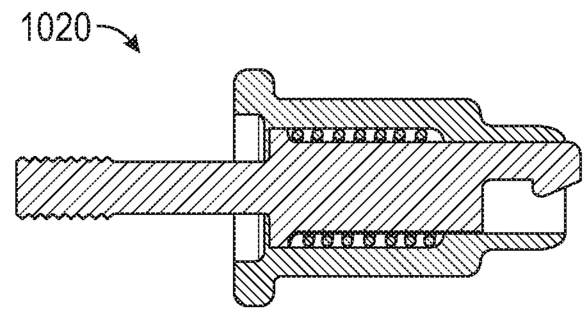
FIG. 10A shows a cross-sectional view of an example of a connector for coupling a main body to a tool.
Figure 10B:
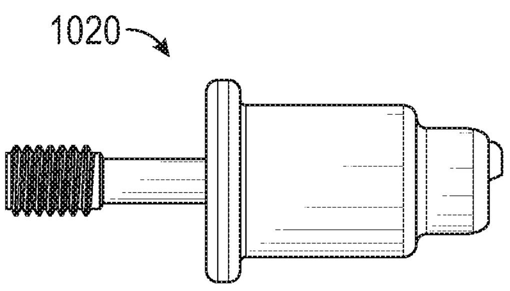
FIG. 10B shows a side view of the example of the connector of FIG. 10A.

FIG. 10A shows a cross-sectional view of an example of a connector 1020 for coupling a main body to a tool. FIG. 10B shows a side view of the example of the connector 1020 of FIG. 10A.

In some examples, the threaded proximal end of the connector 1020 can couple with a threaded hole of a main body, or slap hammer. The distal end of the connector 1020 can couple with a variety of tools. The tools can couple with the distal end of the connector 1020 as described with respect to other connectors herein.

Figure 11A:
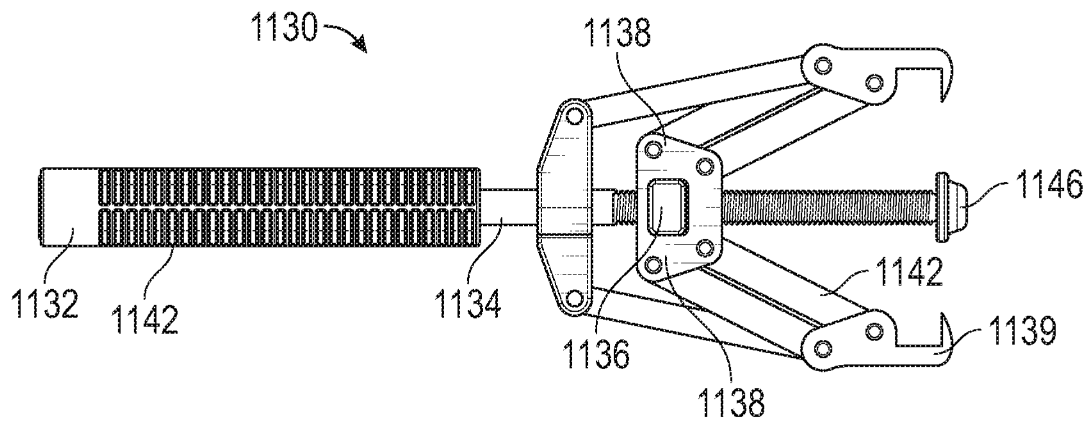
FIG. 11A shows another example of a knee extractor with a synchronizer in a locked position.
Figure 11B:
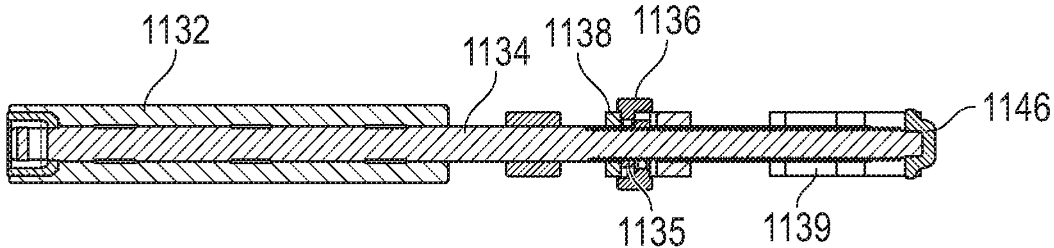
FIG. 11B shows a cross-sectional, side view of the knee extractor of FIG. 11A with the synchronizer in a locked position.
Figure 11C:
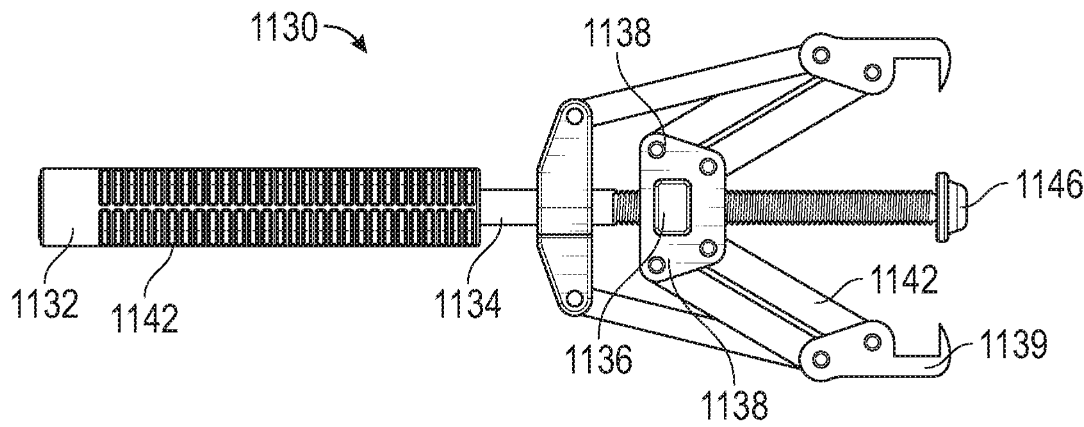
FIG. 11C shows the example of the knee extractor of FIG. 11A with the synchronizer in an unlocked position.
Figure 11D:
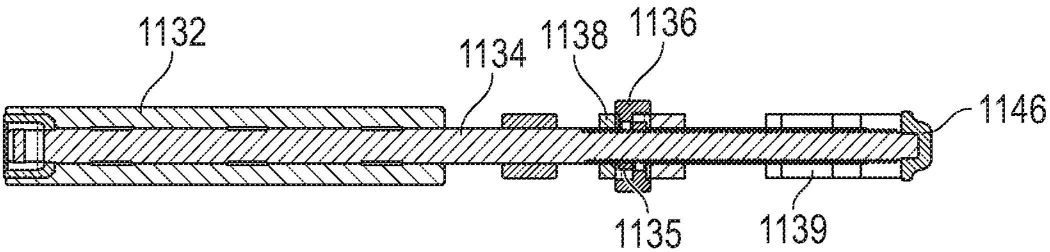
FIG. 11D shows a cross-sectional, side view of the knee extractor of FIG. 11A with the synchronizer in an unlocked position.
Figure 11E:
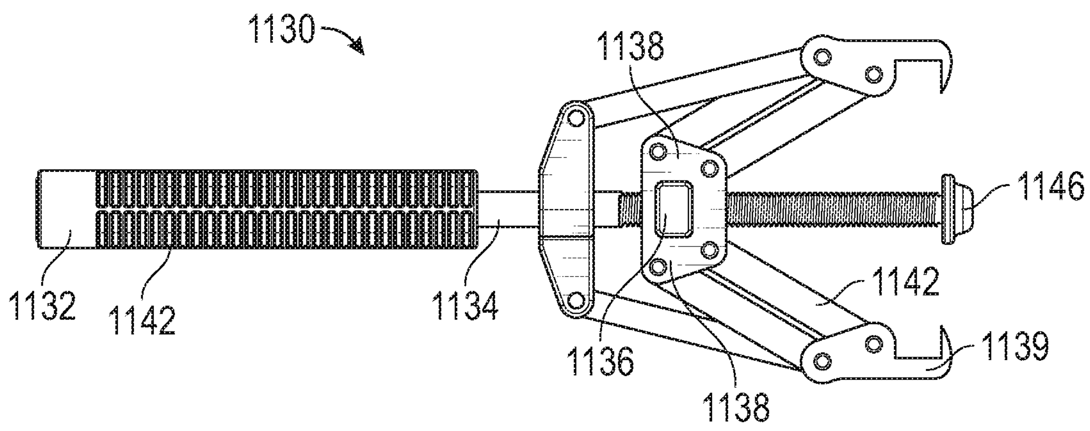
FIG. 11E shows the example of the knee extractor of FIG. 11A with the synchronizer in an unlocked, actuated position.
Figure 11F:
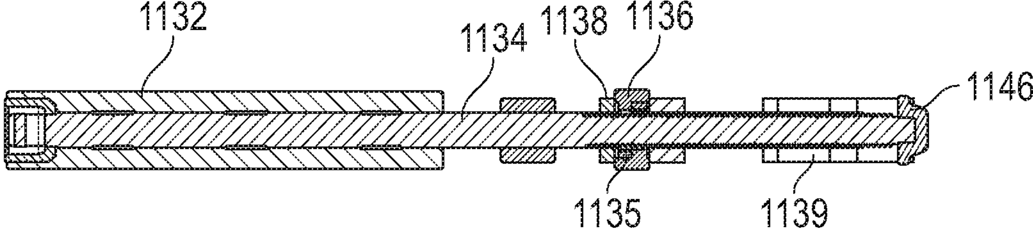
FIG. 11F shows a cross-sectional, side view of the knee extractor of FIG. 11A with the synchronizer in an unlocked, actuated position.
Figures 11G, 11H:
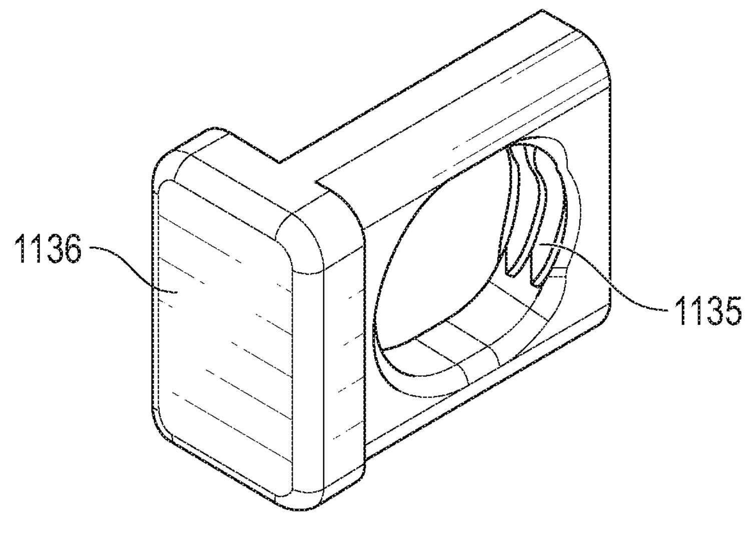
FIGS. 11G-11H show the synchronizer of the example of the knee extractor of FIG. 11A.

FIG. 11A shows another example of a knee extractor 1130 with a synchronizer 1136 in a locked position. FIG. 11B shows a cross-sectional, side view of the knee extractor 1130 of FIG. 11A with the synchronizer 1136 in a locked position. FIG. 11C shows the example of the knee extractor 1130 of FIG. 11A with the synchronizer 1136 in an unlocked position. FIG. 11D shows a cross-sectional, side view of the knee extractor 1130 of FIG. 11A with the synchronizer 1136 in an unlocked position. FIG. 11E shows the example of the knee extractor 1130 of FIG. 11A with the synchronizer 1136 in an unlocked, actuated position. FIG. 11F shows a cross-sectional, side view of the knee extractor 1130 of FIG. 11A with the synchronizer 1136 in an unlocked, actuated position. FIGS. 11G-11H show the synchronizer 1136 of the example of the knee extractor 1130 of FIG. 11A.

The knee extractor 1130 can include any of the features of and/or be coupled with elements of the total knee extraction systems and connectors described with respect to FIGS. 1A-1C, 2A-2C, 3, 4A-4C, 5A-5B, 6, 7A-7B, 8A-8B, 9A-9B, and 10A-10B.

In some examples, the knee extractor 1130 can include a shaft 1134 distal to the connection component 1132. The shaft 1134 can be at least partially threaded. In some implementations, rotating an actuator can cause the shaft 1134 to rotate. The knee extractor 1130 can include a synchronizer 1136, or release button. The synchronizer 1136 can have a clearance hole through the center, such that the synchronizer 1136 has no attachment to the rod. In some examples, the connection component 1132 can be ribbed or have recesses to enhance ease of use, or improve a user's grip.

In some examples, the knee extractor 1130 can include a midplate 1138. In some implementations, the midplate 1138 can move along the shaft 1134 as the shaft 1134 rotates. In some examples, the knee extractor 1130 can include grippers 1144. The grippers 1144 can be connected to the midplate 1138 and/or the synchronizer 1136 by beams 1142. In some implementations, each gripper can be connected to the midplate 1138 by 2 beams. In some implementations, each gripper can be connected to the midplate 1138 by 1-5 beams. In some implementations, each gripper can be connected to the synchronizer 1136 by 1 beam. In some implementations, each gripper can be connected to the synchronizer 1136 by about 1-5 beams. The knee extractor 1130 can include a shaft cap 1146. The shaft cap 1146 can prevent the midplate from moving past the distal end of the shaft 1134.

In some examples, synchronizer 1136 can be engaged or released to release a partial thread 1135 of the synchronizer 1136 from the thread of the shaft 1134. In some examples, the synchronizer 1136 can be locked such that the synchronizer 1136 cannot be engaged without unlocking the synchronizer 1136. In some implementations, as shown in FIGS. 11A-11B, the synchronizer 1136 can be in a locked and unreleased position when the synchronizer 1136 is uncompressed and misaligned with an opening in the midplate 1138. The midplate 1138 can prevent the synchronizer 1136 from being inadvertently compressed. In some examples, when the synchronizer 1136 is locked and unreleased, the synchronizer 1136 can be prevented from moving along the shaft 1134 as the shaft 1134 rotates. The synchronizer 1136 can have a partial thread 1135 that engages a thread of the shaft 1134 to prevent movement of the synchronizer 1136 with respect to the shaft 1134. In some examples, this can prevent the beams 1142 or grippers 1144 from moving with respect to the shaft 1134.

In some implementations, as shown in FIGS. 11C-11D, the synchronizer 1136 can be in an unlocked and unreleased position when the synchronizer 1136 is uncompressed and aligned with an opening in the midplate 1138. The opening in the midplate 1138 can allow the synchronizer 1136 to be compressed. In some examples, when the synchronizer 1136 is unlocked and unreleased, the synchronizer 1136 can be prevented from moving along the shaft 1134 as the shaft 1134 rotates, as the partial thread 1135 engages a thread of the shaft 1134 to prevent movement of the synchronizer 1136 with respect to the shaft 1134. In some examples, this can prevent the beams 1142 or grippers 1144 from moving with respect to the shaft 1134.

In some implementations, as shown in FIGS. 11E-11F, the synchronizer 1136 can be in an unlocked and released position when the synchronizer 1136 is compressed, or depressed, and aligned with an opening in the midplate 1138. The opening in the midplate 1138 can allow the synchronizer 1136 to be compressed. In some examples, when the synchronizer 1136 is unlocked and released, the synchronizer 1136 can be allowed to move along the shaft 1134 as the shaft 1134 rotates, as the partial thread 1135 is not engaged with the thread of the shaft 1134. In some examples, this can allow the beams 1142 or grippers 1144 to move with respect to the shaft 1134.

In some examples, one synchronizer 1136, or release button, with a partial thread 1135 can be disposed around the shaft 1134. In some examples, two synchronizers 1136, or release buttons, with partial threads 1135 can be disposed around the shaft 1134. The two synchronizer 1136 can be on opposite faces of the midplate 1138. In some examples, each synchronizer 1136 can include holes and/or projections configured to fit with the other synchronizer 1136. In some examples, as shown in FIGS. 11G-11H, the portion of the synchronizer 1136 with the partial thread 1135 can be an opening in a body portion extending from the release button portion. In some examples, the opening of the body portion of the synchronizer 1136 can be circular, ovoid, square, rectangular, or triangular. In some examples, the body portion of the synchronizer 1136 can be misaligned with a central axis of the release button portion of the synchronizer 1136. In some examples, 3-5 synchronizers 1136, or release buttons, with partial threads 1135 can be disposed around the shaft 1134.

Non-Limiting Examples

Example 1. A system for total knee replacement comprising: a main body comprising an actuator configured to move a tool with respect to the main body; a connector, a proximal end of the connector configured to couple to a distal end of the main body, a distal end of the connector comprising a first engagement component; and the tool having a proximal end and a distal end, the tool comprising a second engagement component on the proximal end of the tool, wherein the tool is at least one of: a curved osteotome; a chisel; a straight osteotome; or a knee extractor, wherein the first engagement component of the connector is configured to couple with the second engagement component of the tool, and wherein the first engagement component of the connector is at least partially surrounded by a spring-loaded sheath, the spring-loaded sheath configured to retract from the first engagement component such that the first engagement component can engage the second engagement component.

Example 1. The system of example 1, wherein the spring-loaded sheath is configured to advance at least partially when the first engagement component is coupled with the second engagement component.

Example 2. The system of any one of examples 1 or 2, wherein the main body is a slap hammer.

Example 3. The system of any one of examples 1-3, wherein the first engagement component is a first hook and wherein the second engagement component is a second hook.

Example 4. The system of any one of examples 1-4, wherein the first engagement component is a hook and wherein the second engagement component is a loop.

Example 5. The system of any one of examples 1-5, wherein the first engagement component is a bayonet key and wherein the second engagement component is a bayonet lock.

Example 6. The system of any one of examples 1-6, wherein the tool is the knee extractor, and wherein actuator of the main body is configured to open and close jaws of the knee extractor.

Example 7. The system of any one of examples 1-7, wherein the first engagement component and the second engagement component are configured to couple with a collar positioned radially around the first engagement component and the second engagement component.

Example 8. The system of any one of examples 1-8, wherein the first engagement component and the second engagement component are configured to couple with an adapter therebetween.

Example 9. The system of any one of examples 1-9, wherein the proximal end of the connector is configured to thread into the distal end of the main body.

Example 10. A kit for total knee replacement comprising: a slap hammer; a connector configured to couple to a distal end of the slap hammer; a curved osteotome comprising a connection component configured to couple to the connector; a chisel comprising a connection component configured to couple to the connector; a straight osteotome comprising a connection component configured to couple to the connector; and a knee extractor comprising a connection component configured to couple to the connector; a curved bone tamp; an oscillating saw blade; and a reciprocating saw blade.

Example 11. A method for total knee replacement, the method comprising: providing a main body, a connector, and a first tool, wherein the first tool is one of a curved osteotome, a chisel, a straight osteotome, or a knee extractor, the first tool comprising a connection component; coupling a proximal end of the connector to a distal end of the main body; and coupling a distal end the connector to the first tool by pushing the connection component of the first tool against a distal end of the connector to cause a spring-loaded sheath on a distal end of the connector to retract, wherein retraction of the spring-loaded sheath unsheathes an engagement component of the connector, the engagement component of the connector configured to couple with an engagement component of the tool.

Example 12. The method of example 12, further comprising disconnecting the connection component of the first tool from the connector.

Example 13. The method of any one of examples 12 or 13, further comprising coupling the connection component of a second tool, wherein the second tool is one of a curved osteotome, a chisel, a straight osteotome, or a knee extractor.

Example 14. The method of any one of examples 12-14, further comprising moving a handle on the main body to actuate the first tool.

Example 15. The method of any one of examples 12-15, wherein coupling the connector to the first tool further comprises engaging a first hook on the connector with a second hook on the first tool.

Example 16. The method of any one of examples 12-16, wherein coupling the connector to the first tool further comprises engaging a hook on the connector with a loop on the first tool.

Example 17. The method of any one of examples 12-17, wherein coupling the connector to the first tool further comprises engaging a bayonet key on the connector with a bayonet lock on the first tool.

Example 18. The method of example 13, wherein disconnecting the connection component of the first tool from the connector comprises disengaging a first hook on the connector from a second hook on the first tool.

Example 19. The method of example 13, wherein disconnecting the connection component of the first tool from the connector comprises disengaging a hook on the connector from a loop on the first tool.

Example 20. The method of example 13, wherein disconnecting the connection component of the first tool from the connector comprises disengaging a bayonet key on the connector from a bayonet lock on the first tool.

Example 21. The method of example 13, wherein disconnecting the connection component of the first tool from the connector comprises: retracting an outer casing of the connector; tilting at least one of the connector or the connection component; and separating the connector and the connection component.

Example 22. The method of any one of examples 12-22, further comprising removing an implant from a knee of a patient using the knee extractor.

Example 23. A knee extractor comprising: a shaft comprising a first thread; a first plate secured to the shaft; a first beam extending from the first plate; a gripper connected to the first beam; a second beam extending from the gripper; a second plate connected to the second beam, the second plate comprising an opening; and a synchronizer disposed at least partially in the opening of the second plate, the synchronizer comprising a clearance hole disposed radially around the shaft, wherein the clearance hole comprises a second thread threaded to engage the first thread of the shaft, such that the second plate is prevented from moving along the shaft when the second thread engages the first thread.

Example 24. The knee extractor of example 24, wherein the synchronizer is movable between a first position where the second thread engages the first thread and a second position where the second thread does not engage the first thread, wherein depressing a surface of the synchronizer moves the synchronizer from the first position to the second position.

Example 25. The knee extractor of example 25, wherein the synchronizer is moveable to a locked position such that the surface of the synchronizer is prevented from being depressed by a portion of the second plate.

OTHER VARIATIONS

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

Conditional language used herein, such as, among others, "can," "could", "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to couple a list of elements, the term "or" means one, some, or all of the elements in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language, such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Headings are included herein for reference and to aid in locating various sections. These headings are not intended to limit the scope of the concepts described with respect thereto. Such concepts may have applicability throughout the entire specification.

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

What is claimed is:

1. A method for connecting an orthopedic tool, the method comprising:

providing a main body, a connector, and a first tool, wherein the first tool is one of a curved osteotome, a chisel, a straight osteotome, or a knee extractor, the first tool comprising a connection component;

coupling a proximal end of the connector to a distal end of the main body; and coupling a distal end of the connector to the first tool by pushing the connection component of the first tool against a distal end of the connector to cause a spring-loaded sheath on a distal end of the connector to retract, wherein retraction of the spring-loaded sheath exposes an engagement component of the connector, the engagement component of the connector configured to couple with an engagement component of the first tool.

2. The method of claim 1, further comprising disconnecting the connection component of the first tool from the connector.

3. The method of claim 2, further comprising coupling the connection component of a second tool, wherein the second tool is one of a curved osteotome, a chisel, a straight osteotome, or a knee extractor.

4. The method of claim 1, further comprising moving a handle on the main body to actuate the first tool.

5. The method of claim 1, wherein coupling the connector to the first tool further comprises engaging a first hook on the connector with a second hook on the first tool.

6. The method of claim 1, wherein coupling the connector to the first tool further comprises engaging a hook on the connector with a loop on the first tool.

7. The method of claim 1, wherein coupling the connector to the first tool further comprises engaging a bayonet key on the connector with a bayonet lock on the first tool.

8. The method of claim 2, wherein disconnecting the connection component of the first tool from the connector comprises disengaging a first hook on the connector from a second hook on the first tool.

9. The method of claim 2, wherein disconnecting the connection component of the first tool from the connector comprises disengaging a hook on the connector from a loop on the first tool.

10. The method of claim 2, wherein disconnecting the connection component of the first tool from the connector comprises disengaging a bayonet key on the connector from a bayonet lock on the first tool.

11. The method of claim 10, wherein disconnecting the connection component of the first tool from the connector comprises:

retracting an outer casing of the connector;

tilting at least one of the connector or the connection component; and separating the connector and the connection component.

* * * * *